(12) United States Patent
Escobar Valdes et al.

(10) Patent No.: US 9,468,215 B2
(45) Date of Patent: Oct. 18, 2016

(54) BIONEMATICIDE COMPOSITION AND METHOD FOR CONTROLLING PHYTOPATHOGENIC NEMATODES USING THE SAME

(71) Applicant: BIO INSUMOS NATIVA SpA, Talca (CL)

(72) Inventors: Paulo Escobar Valdes, Talca (CL); Eduardo Donoso Cuevas, Talca (CL); Gustavo Lobos Prats, Talca (CL)

(73) Assignee: BIO INSUMOS NATIVA SpA, Malue Talca (CL)

( * ) Notice: Subject to any disclaimer, the term of this patent is extended or adjusted under 35 U.S.C. 154(b) by 0 days.

(21) Appl. No.: 14/168,519

(22) Filed: Jan. 30, 2014

(65) Prior Publication Data
US 2014/0212376 A1    Jul. 31, 2014

(30) Foreign Application Priority Data

Jan. 30, 2013  (CL) .................................. 00307-2013

(51) Int. Cl.
| | | |
|---|---|---|
| A01N 63/00 | (2006.01) | |
| A01N 25/08 | (2006.01) | |
| C12R 1/085 | (2006.01) | |
| C12R 1/07 | (2006.01) | |
| C12N 1/20 | (2006.01) | |

(52) U.S. Cl.
CPC ................. *A01N 63/00* (2013.01); *C12N 1/20* (2013.01); *C12R 1/075* (2013.01); *C12R 1/085* (2013.01)

(58) Field of Classification Search
None
See application file for complete search history.

(56) References Cited

U.S. PATENT DOCUMENTS

| | | | |
|---|---|---|---|
| 2011/0033436 A1* | 2/2011 | Chen et al. ............. | 424/93.461 |
| 2011/0064718 A1 | 3/2011 | Campos et al. | |
| 2012/0003197 A1 | 1/2012 | Jacobsen et al. | |

FOREIGN PATENT DOCUMENTS

| | | |
|---|---|---|
| CN | 101054565 A | 10/2007 |
| CN | 101884326 A | 11/2010 |
| EP | 1046338 A1 | 10/2000 |
| WO | WO 2007/149817 A2 | 12/2007 |
| WO | WO 2009/031874 A1 | 3/2009 |
| WO | WO 2011/121408 A1 | 10/2011 |
| WO | WO 2012/020014 A1 | 2/2012 |
| WO | WO 2012/038480 A2 | 3/2012 |

OTHER PUBLICATIONS

Arias, A.P. "Plant parasitic nematodes: Trainers nematodes, tactics for handling", http://www.monografias.com/trabajos75/nematodos-fitoparasitos-manejo-formadores-agallas/nematodos-fitoparasitos-manejo-formadores-agallas.shtml. Downloaded Nov. 26,2015. (and Google translation).

Atkins et al., "The use of real-time PCR and species-specific primers for the identification and monitoring of Paecilomyces lilacinus", FEMS Microbiology Ecology (2005), 51: 257-264.

Berkalaar, P.E., "Nematode Management Methods" ECHO Development Notes (2002), 75: 1-7. (English translation).

Braga, R. et al., "(Manual para la Capacitacion de Trabajadores de Extension y Agricultores—Alternatives al Bromuro de Metilo para la Fumigacion de los Suelos")", "Training Manual for Extension Workers and Farmers—Methyl Bromide Alternatives for Soil Fumigation", Unity of Action for Ozone and Energy, UNEP and FAO, Rome (2003), (English Abstract), 83 pages.

Ciancio, A. et al., "Ecology and biodiversity of *Pasteuria* spp., Natural antagonists of nematodes fitoparasiticos". Venezuelan Phytopathology (1998), 11 (1): 2-9. (English Abstract on p. No. 8).

Dong and Zhang, "Microbial control of plant-parasitic nematodes: a five-party interaction", Plant Soil (2006), 288: 31-45.

Fernandez, E., "Manejo De Fitonematodos En La Agriculture Cubana" ("Phytonematodes Management in Cuban Agriculture"), FITOSANIDAD (2007), 11(3): 57-60 (English Abstract).

Giannakou, I.O. et al., "Aspects on the attachment of Pasteuria penetrans on root-knot nematodes", Russian Journal of Nematology (2002), 10(1): 25-31.

Hernandez, M.A. and Hidalgo-Diaz, L., "KlamiC®: Bionematicida Agrícola Producido a Partir Del Hongo *Pochonia chlamydosporia* var. catenulata", (KlamiC®: Produced Agricultural Nematicide from the fungus *Pochonia chlamydosporia* var. catenulata), Rev. Protección Veg. (2008), 23(2): 131-134. (English Abstract).

Holland, R.J. et al., "Infection of Meloidogyne javanica by Paecilomyces lilacinus", Nematology (1999), 1(2): 131-139.

Jonathan, E.I. et al., "Field application of Paecilomyces lilacinus for the Control of Meloidogyne incognita on betelvine, Piper betle", Nematol. Medit. (2000), 28(2): 131-133.

Kerry, B.R.: "Exploitation of the Fungus Verticillium Nematophagous chlamydosporium Goddard for the Biological Control of Root-knot nematodes (*Meloidogyne* spp.)", Fungi as Biocontrol Agents: Progress, Problems and Potential (2001), (Butt, T M, Jackson, C and Magan, N, Eds) CABI International, Wallingford Chapter 5: 155-168,24 pages.

Labrada, R. and Fornasari, L. (Eds): "Global Report on Validated Alternatives to the Use of Methyl Bromide for Soil Fumigation", FAO and UNEP (2001), 93 pages.

Meyer, S.L.F. and Roberts, D.P. "Combinations of Biocontrol Agents for Management of Plant-Parasitic Nematodes and Soilborne Plant-Pathogenic Fungi", Journal of Nematology (2002), 34(1): 1-8.

(Continued)

*Primary Examiner* — Robert T Crow
*Assistant Examiner* — John P Nguyen
(74) *Attorney, Agent, or Firm* — Cooley LLP

(57) ABSTRACT

The present invention relates to the field of biotechnology, and particularly relates to a bionematicide composition broad spectrum action on phytopathogenic nematodes which comprises one or more bacterial strains isolated from Chilean soil belonging to the genus *Bacillus*, and the method of use of this composition for the protection of plants against nematode attack.

25 Claims, 6 Drawing Sheets

(56) References Cited

OTHER PUBLICATIONS

Rojas, R.M., "Economic analysis of alternatives to combat nematodes in rice cultivation (*Oryza sativa*)", Technological Scope, Rev. the National Institute of Agricultural Innovation and technology Transfer (2003), 1 (1): 26-29). (Google translation, Abstract).

Rojas, M. T. and Marban-Mendoza, N., "Pasteuria penetrans: Adherencia y Parasitismo en Meloidogyne incognita y Meloidogyne arabicida", Nematropica (1999), 29: 233-240 (English Abstract).

Schenck, S. "Control of Nematodes in Tomato with *Paecilomyces lilacinus* Strain 251," Hawaii Agriculture Research Center, Vegetable Report 5 (2004), pp. 1-5.

Trudgill, D.L. and Blok, V.C., "Apomictic, polyphagous root-knot nematodes: exceptionally successful and damaging biotrophic root pathogens," Annu. Rev. Phytopathol. (2001), 39: 53-77.

* cited by examiner

BIONEMATICIDE COMPOSITION AND METHOD FOR CONTROLLING PHYTOPATHOGENIC NEMATODES USING THE SAME

CROSS REFERENCE OF RELATED PATENT APPLICATION

This application claims priority to Chilean Patent Application CL 00307-2013, filed Jan. 30, 2013, which is hereby incorporated by reference in its entirety for all purposes.

BACKGROUND OF THE INVENTION

Among the pests that affect agriculture and livestock sectors, the nematodes are responsible for substantial losses in many crops worldwide scale (Rojas. T.: "Economic analysis of alternatives to combat nematodes in rice cultivation (*Oryza sativa*)", Technological Scope, Rev. the National Institute of agricultural Innovation and technology Transfer 1 (1): 21-24). If we add that, in addition to the direct damage that these organisms cause, they often leave access doors for the establishment of fungi, bacteria and viruses, these damages could reach higher magnitudes.

Among the phytopathogenic nematodes those of the genus *Meloidogyne* are considered the most economically important worldwide for the damage they cause, characterized by a significant reduction in yields and the large number of plant species they attack, including most vegetables, viands, fruit, ornamental and weed flora (Trudgill, D L and Blok, V C: "apomictic polyphagous root-knot nematodes: exepcionally successful and damaging biotrophic root pathogens." Phytopathol Ann Rev., 39: 53-77, 2001).

Although today it is clear the potential harm that nematodes pose to agriculture in general, there are still difficulties regarding their control. Traditionally it have been used different control alternatives to reduce and/or eliminate nematode populations (Berkelaar, E.:. "Nematode Management Methods" ECHO Development Notes, 75: 1-6. 2002). For many years, it have been used in an irrational way, a wide range of chemical nematicides, many of which are biocides with a negative impact impact on beneficial organisms in the soil. Also, the harmful impact they cause to human health and the environment in general, have limited their use worldwide (Labrada, R. and Fornasari, L. (Eds): "Global Report on Validated Alternatives to the Use of Methyl bromide for Soil Fumigation "FAO-UNEP, p 86, 2001, Braga, R., Labrada, R. . . . Fornasari, L. Fratini, N." Training Manual for Extension Workers and Farmers-Methyl Bromide Alternatives for Soil Fumigation. "Unity of Action for Ozone and Energy, UNEP-FAO, Rome, 74 p., 2003).

Biological pest control includes strengthening the natural control, the introduction of nonnative species and the use of pesticides derived from animals, plants, fungi, bacteria and viruses to prevent, repel, remove or reduce the damage caused by pests (Carballo, M. and Guaharay, F. (Eds.). "Biological Control of Agricultural Pests" Technical Series, Technical Manual Tropical. Agricultural Research and Education center, 53: 224, 2004).

Despite its effectiveness, biopesticides are only a small percent of the global pesticide market, every day aspect that is being given more and more importance as the use of biological organisms is a more environmentally friendly alternative and in the particular case of plant parasitic nematodes, although many microorganisms are their antagonists and those are the principal group of biopesticides, very few of them are commercially available, mainly due to the inconsistent results obtained in mass production and application thereof (Meyer, Susan and Roberts, DP: "Combinations of Biocontrol Agents for Management of Plant-Parasitic Nematodes and Plant-Pathogenic Fungi soilborne" Journal of Nematology, 34 (1) :1-8, 2002).

Among the main microbial groups with potential as biological control agents of nematodes are bacteria and fungi., being prominent among them, *Pasteuria penetrans* (Thorne) Sayre and Starr Ciancio, A., Carbonell, E. and Crozzoli, R. "Ecology and biodiversity of *Pasteuria* spp., Natural antagonists of nematodes fitoparasiticos". Venezuelan Phytopathology, 11 (1): 1-9, 1999, Rojas, M. T. and Marban-Mendoza, N.: "*Pasteuria penetans* Adherence and parasitism in *Meloidogyne incognita* and *Meloidogyne arabicida*". Nematropica, 29: 233-240, 1999; Giannakou, I. O.; Gowen, S. R. and. Davies, K. G.: "Aspects on the attachment of *Pasteuria penetans* on root-knot nematodes." Russian Journal of Nematology, 10: 25-31, 2002), *Tsukamurella paurmetabola* (Steinhaus) strain C924, recently registered as Appropriate Urban Agriculture Alternatives "In: Course on Urban Agriculture, p 121-139 Spanish International Cooperation Agency INIFAT Havana, 1997, Fernandez, E." Susceptibility of varieties of potato (*Solanum tuberosum* L .) to Cuban populations of *Meloidogyne* spp "Phytosanitary, 3 (3): 109-112, 1999; *Paecilomyces lilacinus* (Thom) Samson (Jonathan, E I.; Arulmozhiyan, R., Muthusamy, S. and Manuel, W W. "Field application of Paecilomyces lilacinus for the Control of *Meloidagyne incognita* on betelvine. Piper betle" Nematol Medit, 28 (2): 131-133, 2000; Schenck, S.:. "Control of Nematodes in Tomato with *Paecilomyces lilacinus* Strain 251 "Hawaii Agriculture Research Center, Vegetable Report, (5). 5, 2004), of which are commercial products such as Biostat (Laverlam) Bioact, and PL plus Paecyl (Holland, R J: "PAECIL" http://www.ticorp.com.au/article1.htm 2001 (accessed May 2004, 136 Holland, R J, Williams K L and Khan, A.: "Infections of the interaction of Paecylomices lilacinus with *Meloidoyne incognita*" Nematology,: 1: 131-139, 1999, 137 Lopez, J A: "Biological Control of Nematodes Plant pests "In: Biological Control of Agricultural Pests (Caraballo, M. and Guaharay, F. Eds): 185-200 Technical Series, Technical Manual Tropical Agricultural Research and Education, 53, 2004, 138 Doug, L Q and Zhang, K Q, "Microbial Control of plant-parasitic nematodes: a five party interaction." Plant Soil, 288: 31-45, 2006) and *P. chlamydosporia* (Goddard) Zare and W. Gams (formerly *Verticillium chlamydosporium* Goddard) (Kerry, B R: "Exploitation of the Fungus *Verticillium Nematophagous chlamydosporium* Goddard for the Biological Control of Root-knot nematodes (*Meloidogyne* spp.)" In: Fungi as Biocontrol Agents: Progress, Problems and Potential (Butt, T M, Jackson, C and Magan, N, Eds) CABI International, Wallingford Chapter. 5: 155-168, 2001), with the IMI SD 187 strain of *P. chlamydosporia* var. *catenulata* has been achieved a technology of mass reproduction, transferable for the development of other fungi as biological control, which has allowed obtaining bionematicide product called KlaimiC® (Hernández, M A and Hidalgo-Diaz, L.: "KlamiC: agricultural bionematicide produced from the fungus *Pochonia chlamydosporia* var *catenulata* "Rev. Protection Veg, 23 (2): 131-134, 2008) Also appears as a commercial product of Valent Biosciences Corporation (formerly Abbott Laboratories) the bionematicide DiTera (whose active ingredient is constituted by the fungus *Myrothecium verrucaria* DITM and all the products (soluble and solid) results of fermentation (Gullino, M. and Benuzzi, M.: "Mezzi biologici e prodotti per la naturale di origine difesa parassiti terricoli dai" Informatore phytopathologic, 10: 51-57, 2003; 142. Lopez, J. A.: "'Biological Control of Nematode Parasites of Plants" In: Biological Control of Agricultural Pests (Caraballo, M. and Guaharay, F. Eds): 185-200 Technical Series, Technical Manual Tropical Agricultural Research and Education center, 53, 2004).

The state of the art shows an increasing number of patent documents that are being published regarding the use of bionematicides for controlling these pests among these may be mentioned the following:

- WO2007149817: Combinations Of Biological Control Agents with a Nematicidal Seed Coating, Applicant Univ California:
- WO2012020014: Nematocidal Composition Comprising *Bacillus subtilis* and *Bacillus licheniformis*, Applicant Chr Hansen as:
- CN101054565: Biological Control Strain Capable Of Preventing And Curing Root Knot Nematode Disease for Greenhouse Vegetable, Applicant Univ Nanjing Agricultural;
- CN101884326: Preparation And Application Technology For Waxy *Bacillus* Suspension Agent, Applicant Zhigao Zhang; Xiaogen Yin;
- EP1046338: Nematicide Agent and Method for the Bio-Control of Nematodes, Applicant Centro De Ingenieria Genetica Y Biotecnologia;
- MX2010002412: Strain of *Bacillus subtilis* for Agricultural Use, Applicant Adntes Lab Sa De C V;
- WO2011121408: Bacterial Strains and a Bionematicide and Plant Growth Stimulator Containing them, Applicant Probelte Sa.
- US20120003197: *Bacillus* isolates and methods of their use to protect against plant pathogens and virus transmission, patent holder MONTANA STATE UNIVERSITY; and
- WO2012038480: Use of biological or chemical control agents for controlling insects and nematodes in resistant crops, applicant BAYER CROPSCIFNCE AG; among others.

While it may be concluded that it is widely known in the state of the art the use of various bacterial strains, and especially of the genus *Bacillus*, for the control of nematodes in plants, it should also be noted that the search for new strains against these pests is still of great interest to agronomists who are confronted daily with the need for effective control of nematodes in crops of interest, employing nematicides agents nontoxic for plants to which they apply and for the users thereof.

SUMMARY OF THE INVENTION

The present invention aims to provide a bionematicide composition intended to control phytopathogenic nematodes in agriculture and forestry plants grown, ornamental, for domestic use and wild plants, which is mainly active against nematodes of the genera *Meloidogyne, Tylenchulus, Pratylenchus, Paratylenchus* and *Xiphinetna*, among others.

The bionematicide composition of the invention is obtained using at least one strain belonging to a group of bacterial strains isolated from Chilean soil, and belonging to the genus *Bacillus* specifically *Bacillus cereus* bacteria Peumo strain deposited in the bank of strains USDA ARS under accession number NRRL B-50767, *Bacillus cereus* Bromelia strain deposited in the bank of strains USDA ARS under the accession number NRRL B-50766 and *Bacillus thuringiensis* Anemophyla strain deposited in the bank of strains USDA ARS under the accession number NRRL B-50765, or fermentation products thereof, and an agronomically acceptable carrier.

In a preferred embodiment of the invention, the bionematicide composition exhibits or more of said strain in the form of spores.

In another preferred embodiment, the bionematicide composition uses an agronomically acceptable excipient which is selected from group consisting of clays, kaolin, talc, zeolite, water, vegetable oils and paraffinic minerals or non-paraffinic minerals.

The invention also relates to formulations of bionematicide composition in form of a capsule, a bait, a concentrate, an emulsion, a suspension, a tablet, a gel, a paste, a gel emulsifiable, dispersible granules, macro granules, micro granules, powder, a solution or other appropriate formulation for application.

It is also envisaged as part of the inventive concept of the proposed technical solution, the use of the composition for the control of various phytopathogenic nematodes.

Another object of the present invention involves a method for the control of phytopathogenic nematodes, in which first is formulated, the composition which comprises the mentioned bionematicide strains and then said formulation is applied to plants or plant parts or seeds thereof, where you want to perform this control.

The compositions of the invention comprising both strains individually and their possible mixtures and formulations allow the control of pests without the use of conventional chemical insecticides, which, by its nature, has no environmental restrictions and can be used in conventional agricultural production, organic or be used in any other certification system.

BRIEF DESCRIPTION OF THE FIGURES

The present invention and their importance will be more apparent from the results obtained with the same, and which are shown in the embodiments and illustrated in the attached drawings, where.

*nita*, which shows that it is the only treatment that achieves levels of vegetative development of the plants above the positive control (inoculated) and similar levels of development of a condition without nematodes.

Figure 6:
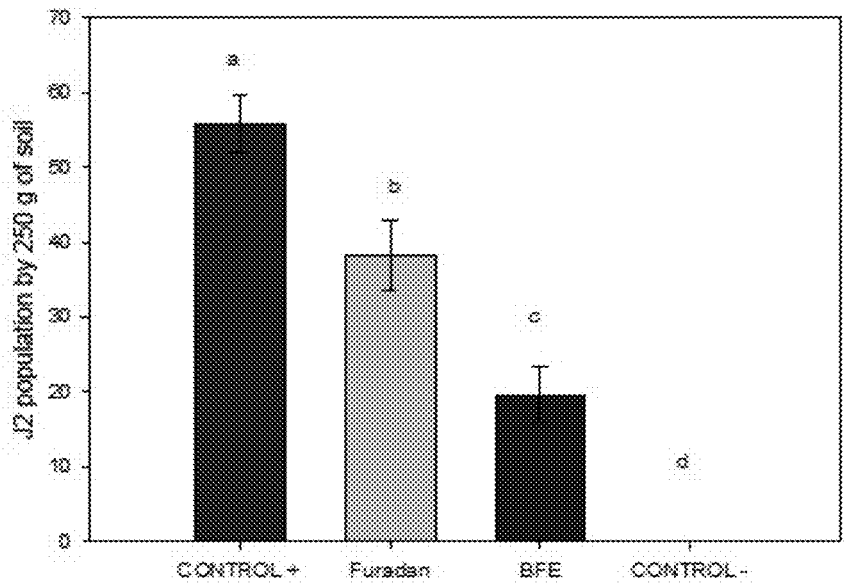

FIG. 6 is a graph showing the nematicidal effect of the BFE blend into doses 2.5 g/l equal to 5 kg/ha, in the final population of juvenile stage (J2) of *Meolidogyne incognita*, on tomato plants in pots, compared to the chemical organophosphorus nematicide tradename Furadan, at the dose recommended by the manufacturer.

Figure 7:
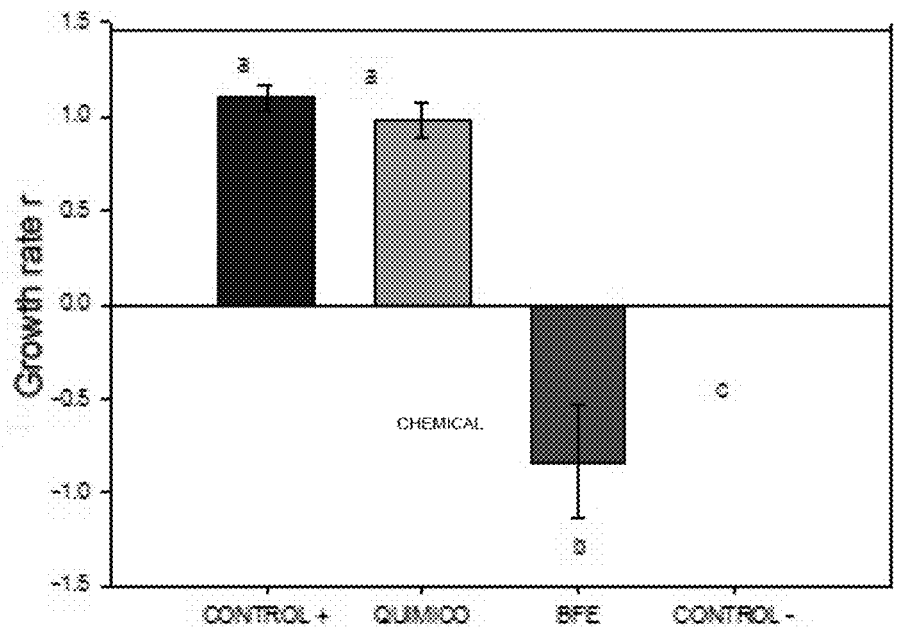

FIG. 7 is a graph where is shown the nematicidal effect of the BFE mixture. at a dosage of 2.5 g/l equal to 5 kg/ha, on the rate of population growth.

Figure 8:
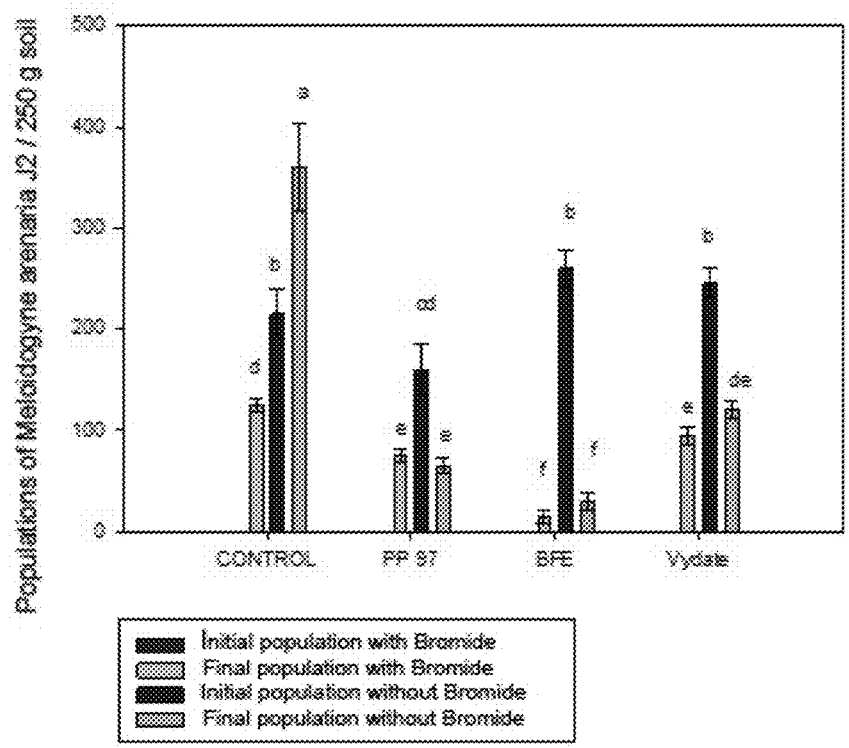

FIG. 8 is a graph showing the effect of of the BFE mixture at a dose of 3 kg/ha, on populations of *Meloidogyne arenaria*, in tomato plants grown in field conditions, with and without the use of methyl bromide in a sandy loam soil.

Figure 9:
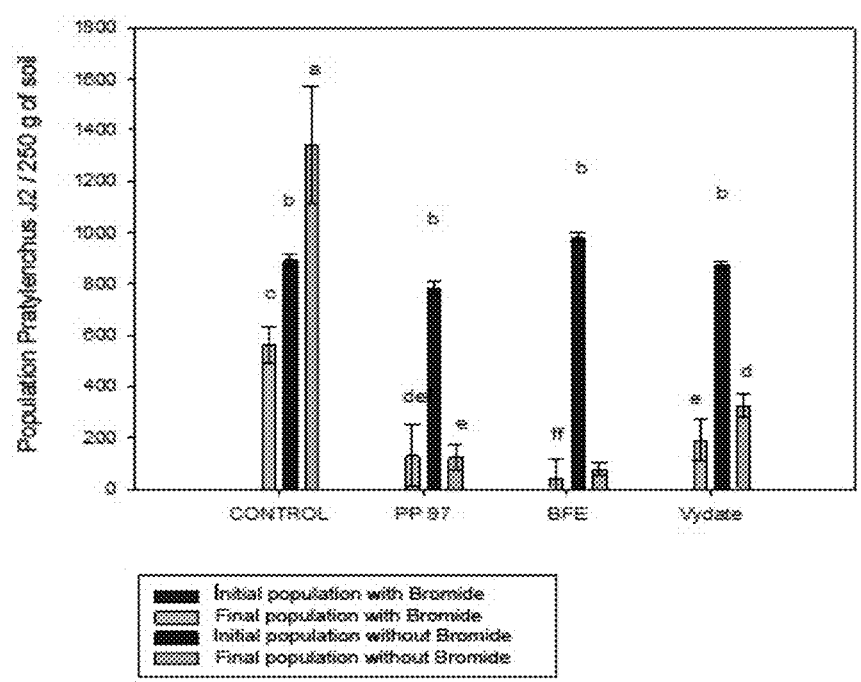

FIG. 9 is a graph showing the effect of of the BFE mixture at a dose of 3 kg/ha, on the population of *Pratylenchus* sp. Tomato plants grown in field conditions, with and without the use of bromide methyl in a sandy loam soil.

Figure 10:
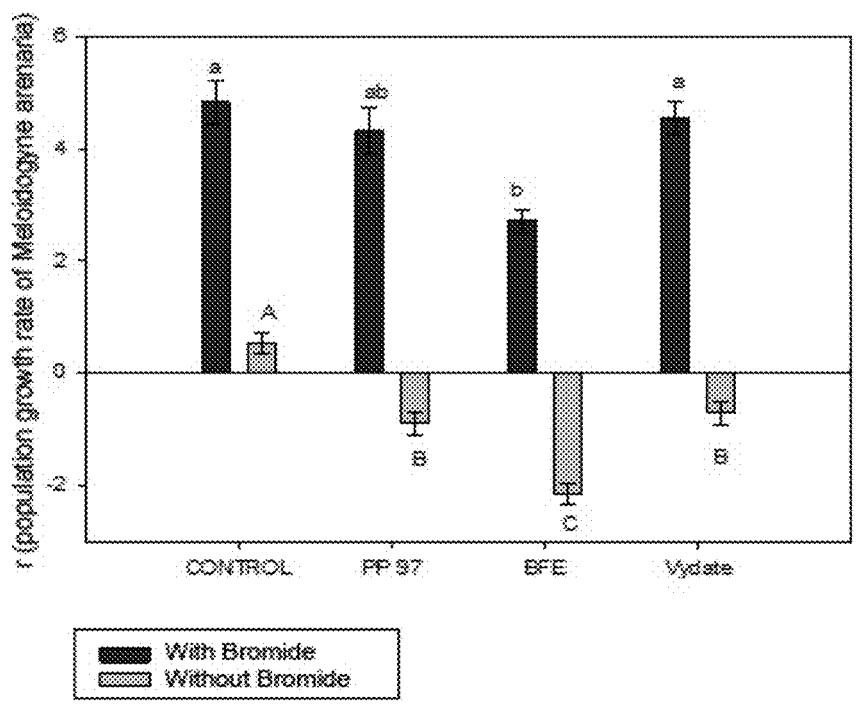

FIG. 10 is a graph showing the effect of of the BFE mixture at a dose of 3 kg/ha, on the rate of population increase of *Meloidogyne arenaria*, in tomato plants grown in field conditions, with and without the use of methyl bromide in a sandy loam soil.

Figure 11:
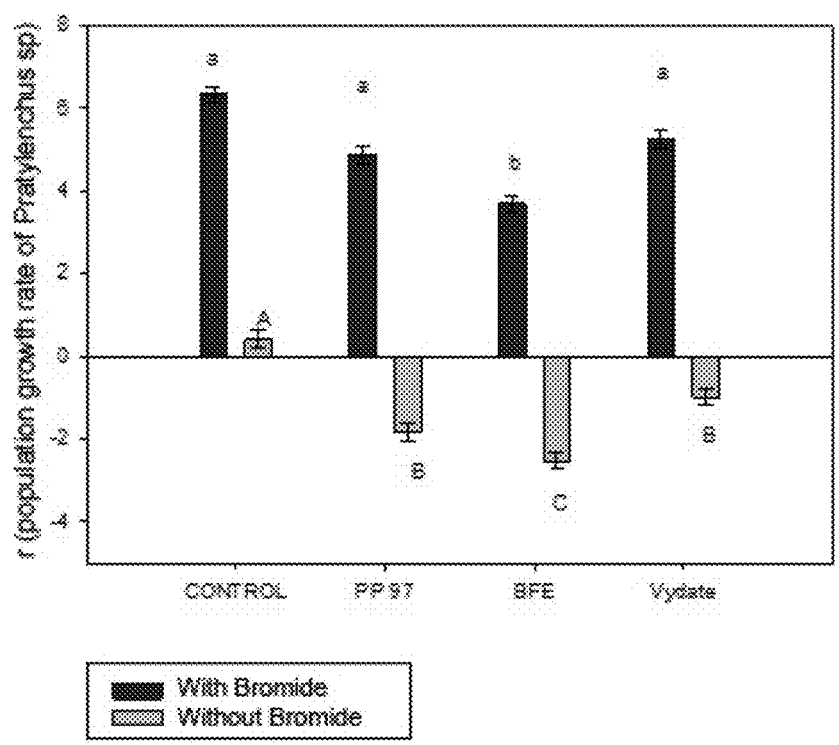

FIG. 11 is a graph showing the effect of of the BFE Mixture at a dose of 3 kg/ha, on the rate of population increase of *Pratylenchus* sp, in tomato plants grown in field conditions, with and without the use of methyl bromide in a sandy loam soil.

DETAILED DESCRIPTION OF THE INVENTION

In the present invention, the following expressions will mean:

Phytopathogenic nematodes: Those species of nematodes that parasitize and feed on living plants in whiCh they produce a wide variety of diseases.

Nematicide: That agent capable of killing nematodes.

Bionematicide: Refers to the agent of biological origin, with the ability to kill nematodes.

Biocontrol: Live Organisms with the ability to reduce the presence or damage of pests and diseases. Among them it can be found animals, fungi, bacteria and viruses.

Intrinsic reproductive rate: Rate of net population increase of plant parasitic nematodes.

Root nodulation: Generation of altered and disordered growth in roots of plants affected by nematodes of the genus *Meloydogine*.

Agronomically acceptable carrier: Refers to any suitable excipient to prepare and/or implement the bioneMaticideS compositions of the invention.

EXAMPLES OF EMBODIMENT

Example 1

Isolation of Strains with Bionematicide Activity from Chilean Soils

For the isolation of the strains, samples of agricultural soils and wild environments were taken from the north end (Parinacota Region) to Cochrane. The samples were processed by routine methods for the extraction of nematodes, which were observed by optical microscopy, selected those who presented alterations in the cuticle (outer layer of skin). These were seeded in selective media for bacteria, based on which these were purified and subsequently cultured in isolated way, for evaluation.

Example 2

Preparation of the Bionematicide Composition

Formula evaluated in the field level, consisted of a mixture of spores obtained based on the fermentation in liquid medium independently of the strains *Bacillus cereus* Peumo strain (NRRL B-50767), *Bacillus cereus* Bromelia strain (NRRL B-50766) and *Bacillus thuringiensis* Anemophyla strain (NRRL B-50765), isolated from Chilean soils according to Example 1, and using the same in equal proportions.

Crops of each Individual strain were monitored to reach about 70-90%, preferably 80% of sporulation in the culture, each strain in culture, was individually, spray dried and heat application to an appropriate carrier (such as kaolin, talc, and the like) after which a population count is made of viable spore through the serial dilution plating on nutrient agar. Once obtained the actual concentrations of each culture, in colony forming units (cfu) after the drying process, the final blend is prepared by adding an inert substrate such as zeolite, talc, kaolinite or vegetable flours, up to reach an optimal concentration 1×108 cfu/g, or around it. This mixture was called BFE.

Example 3

Evaluation of Spore-Forming Bacteria with Nematicidal Activity in in vivo conditions About 4 Species of Phytopathogenic Nematodes On Petri dishes with 10 ml of sterile water. 80 individuals were added of *Meloidogyne incognita* in J2 state, on which different treatments were applied consistent in the 3 strains *Bacillus cercus*Peumo strain (NRRL B-50767), *Bacillus cereus* strain *Bromelia* (NRRL B-50766) and *Bacillus thuringiensis* Anemophyla strain (NRRL B-50765) separately, and the mixture thereof (BFE), adding 1 ml of a spore suspension in a matrix of clay at a concentration of 108 cfu/g of each of the strains at different doses (treatments with 0 (control), 0.5, 1, 1.5 and 3 g/l of the suspension). The plates were incubated for 72 hours with stirring, after which the population of J2 survivors was determined and the presence of endospores attached to juvenile stages of phytopathogenic nematodes was observed.

The same procedure was performed to *Tylenchulus semipenetrans* nematodes, using in this case 450 J2 plate and *Pratylenchus* sp using 120 J2 / plate.

The results obtained based on these experiments are shown in FIG. 3. As can be seen therein, all the bacterial strains were able to reduce populations of nematodes tested in a significant way compared with the untreated control, showing a clear dose-dependent effect. Surprisingly it was observed that the mixture of strains, allows to reduce, significantly and also showing a synergistic effect, the populations of the phytopathogenic nematodes, differing of the treatments with strains used in isolated way, in particular in the lower concentrations.

Example 4

Control *Meloidogyne incognita* by a Mixture of Bacteria with Nematicidal Activity (BFE), Compared with Nematophagous Fungi Under Controlled Conditions of Sandy Soil Tomato plants cv. PATTERN ® of 4 weeks old were transplanted to pots of 8 liters with sterile substrate comprising sand, compost, perlite and peat 2:1:1:1, generating a clay texture soil.

Three days before transplanting, each pot with the respective treatment was inoculated with 2000 eggs of *Meloidogyne incognita*.

Treatments used are referenced in the following Table 1:

TABLE 1

| Treatment | |
|---|---|
| Positive control (+) | Control treatment with only application of nematodes |
| Negative control (−) | Control treatment without the presence of nematodes or control agent |
| BFE mix | Nematicides bacteria mixing application at a dose of 1.5 g/l, equivalent to 3 kg/ha |
| Diterra ® | Commercially available product obtained from the fungus *Myrothecium verrucaria*. Dose recommended by the manufacturer Equivalent to 4 kg/ha |
| Micosplag | Commercially available product, made from the biological control *Metarhizium anisopliae* strain Cenicafe Ma 9236, *Bauveria bassiana* Cenicafe strain Bb 9205 and *Paecilomyces lilacinus* Cenicafe Pl9301, at dose of 300 g/ha. |

After 8 weeks from the application of the treatments, the population of *M. incognita* developed in each pot with their respective treatment was determined using a Baermann funnel also determining the level of nodulation in the roots and the aerial and radicular weight of the plants.

Figure 1:
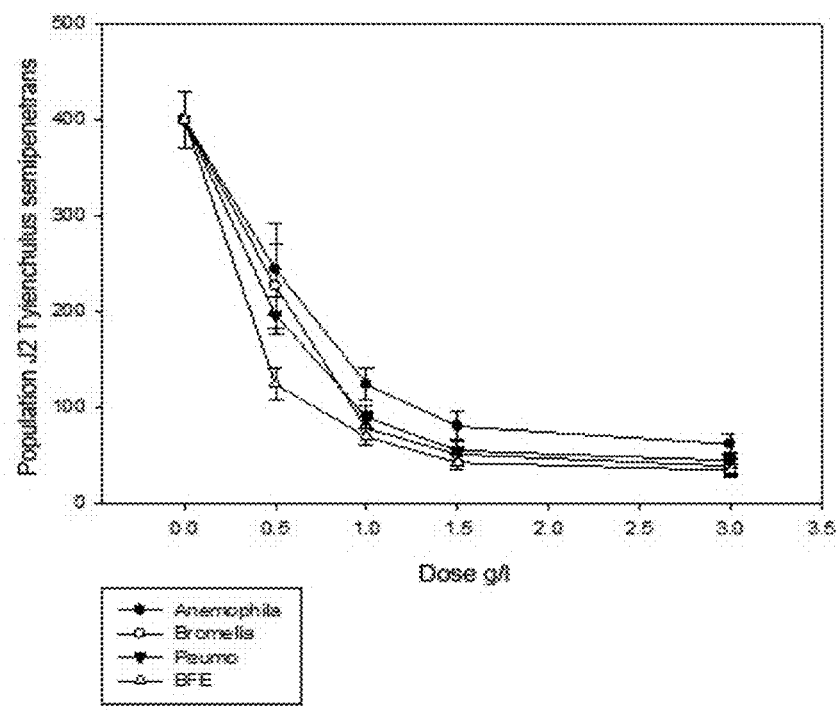
FIG. 1 is a graph showing the nematicidal effect of the different strains and their mixture (BFE) in doses of 0.5 to 3 g/l on populations of juvenile stage (J2) of *Tylenchuhis semipenetrans*, under in vitro conditions, where can be observed that all strains possess nematicidal action in doses above 0.5 g/l providing treatment with the mix BFE, the higher mortality at lower doses.
Figure 2:
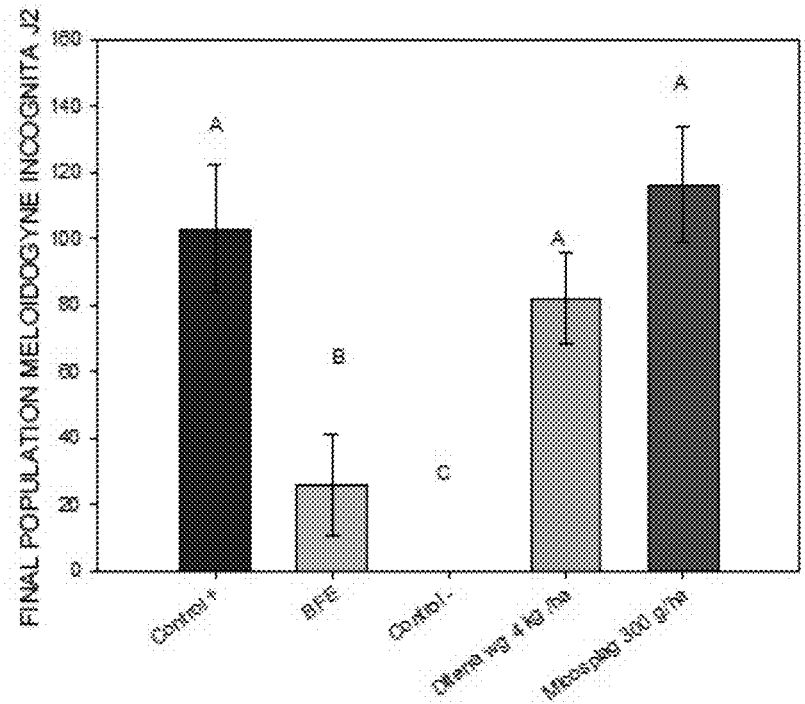
FIG. 2 is a graph showing the nematicide effect of BEE mixture in dose of 1.5 g/l equivalent to 3 kg/ha on the final population of juvenile stage (J2) of *Meolidogyne incognita* in tomato plants in a pot, compared to commercially available products obtained from nematode biocontrol fungi.
Figure 3:
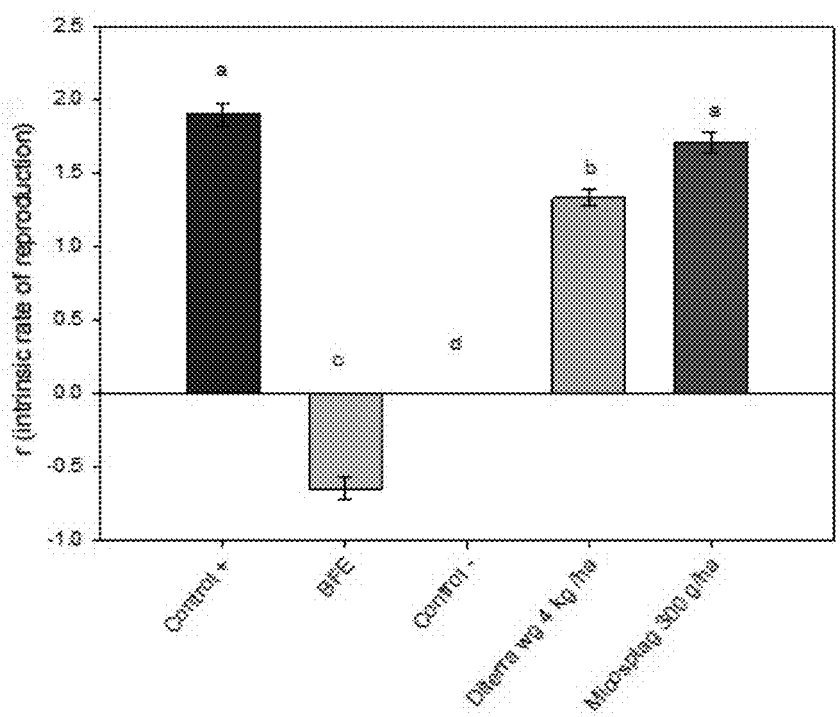
FIG. 3 is a graph showing the effect of nematicide BFE mixture in dose of 1.5 g/l, equivalent to 3 kg/ha on the intrinsic growth rate (LN, final population/initial population) of *Meolidogyne incognita* in potted tomato plants compared to commercially available products, obtained from biocontrol fungi nematodes, where can be observed that the BFE mixture is able to achieve negative population growth rates.
Figure 4:
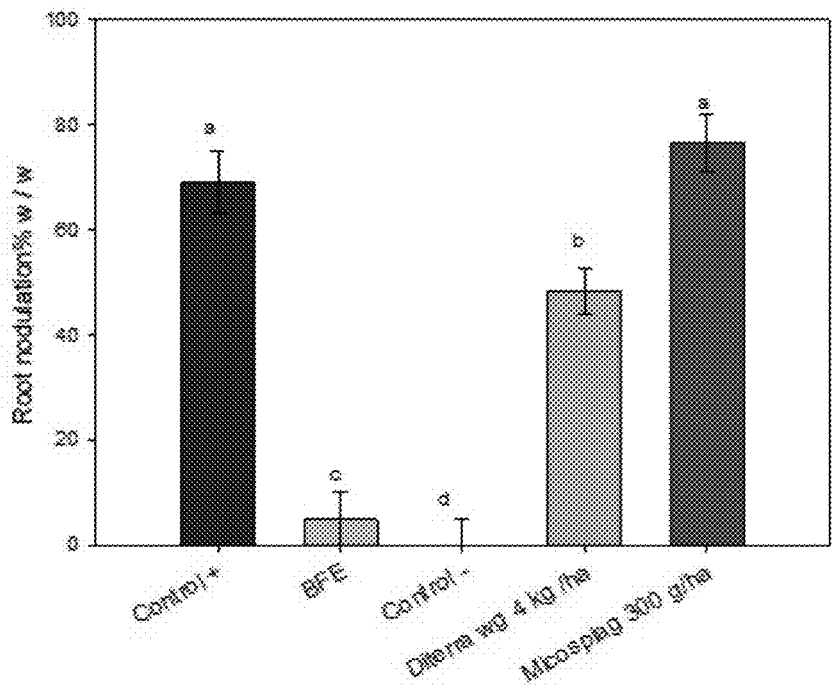
FIG. 4 is a graph showing the effect of the nematicide mixture BFE in dose of 1.5 g/l on the percentage of roots affected by nodes of *Meolidogyne incognita* on potted tomato plants, compared to commercially available products, obtained from nematodes biocontrol fungi.

It was noted that the application of BFE mixture, was able to reduce significantly the size (FIG. 2) and growth rate (FIG. 3) of the population of *Meloidogyne*, differing significantly from both the positive control and commercial biological product used, finding that only treatment with BFE achieved negative population growth rates. It wa also achived a significant decrease in the percentage of nodules (P/P) in treatment with BFE, differentiating of the positive control, as well as commercial biological control agents (P<0.01), and showing no significant differences with negative control, equivalent to a soil without nematodes (FIG. 4).

Figure 5:
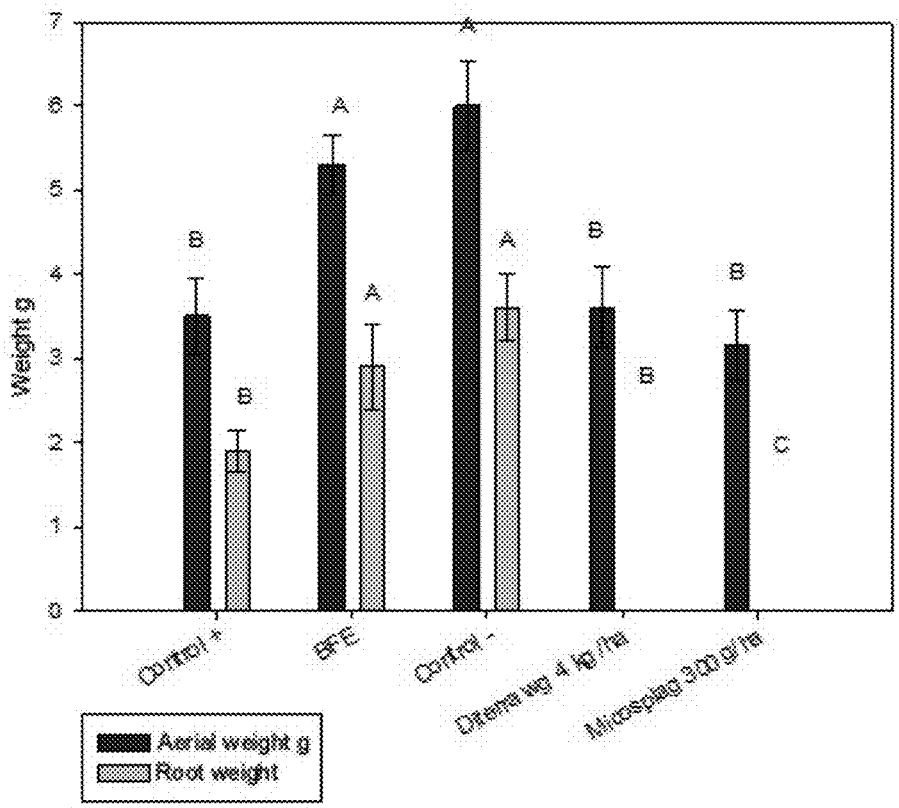
FIG. 5 is a graph showing the effect of BFE, on the aerial and radicular weight of tomato plants grown in pots under controlled conditions, inoculated with *Meloidogyne incog-*

Regarding the impact on plant development, the BFE mixture showed the levels of vegetative development of the plants similar to conditions of absence of nematodes (control −), differentiating significantly from both the control + as well as commercial products (P<0, 05) (FIG. 5).

Example 5

Control of *Meloidogyne incognita* by the Mix of Bacteria with Nematicidal Activity (BFE) in Comparison with a Chemical Nematicide, Under Controlled Conditions Loam Soil In this field test we used a population of *Meloidogyne incognita* identified by perineal cuts obtained of the Colin property also being used the same variety of tomato cv. Maria Italia.

Plants of 4 weeks of age were transplanted to pots of 10 liters, with a sterile substrate that comprises sand, compost perlite, and peat 1:2:2:2, generating a loam texture substrate, corresponding to a soil with features intermediate between clayey and sandy.

Three days befOre transplanting, each pot with their respective treatment was inoculated with 2000 individuals of *Meloidogyne incognita* in the juvenile stage (J2), representing a medium high level of infection The following treatments were applied immediately after transplantation.

Negative control (−): just sterile soil

Positive control (+): Inoculation with nematode

BFE mixture in dose of 50 ml/plant, at a concentration of 2.5 g/liter ($1\times10^8$ spores/g Equivalent to 5 kg/ha.

Chemical control, FURADAN ® (carbofuran) 3 ml/100 ml / pot, equivalent to the commercial dose of 45 l / ha The application of the treatments was performed immediately following transplantation, 2 hours later each plant was inoculated with 3000 J2 of *M. incognita*, representing this a very high level of infection, with the objective of increasing the requirement over the products and make a better evaluation of their effectiveness.

The evaluations were performed 12 weeks after application of the different treatments, consisting of measurements of the population and population growth rate. The nodulation index was calculated on the basis of the provisions in the following Table 2.

TABLE 2

| Nodulation index | Percentage |
|---|---|
| 0 | No presence of nodules |
| 1 | Between 1-10% w/w of nodules |
| 2 | Between 11-30% w/w of nodules |
| 3 | Between 31-50% w/w of nodules |
| 4 | Between 51-70% w/w of nodules |
| 5 | Between <70% w/w of nodules |

In this assay, it was observed that the mixture BFE managed to significantly reduce both population *Meloidgyne* P<0.05 (FIG. 6), as well as its growth rate P<0.05 (FIG. 7), with even higher that achieved by the chemical nematicide Furadan. As for the effect on the roots, it can be seen in FIG. 8, a significant reduction of the nodulation, P<0.01.

Table 3 below summarizes the effect of the BFE mixture on the nodulation ratio of tomato plants grown in pots, caused by *Meolidogyne incognita*, in comparison with the chemical organophosphorus nematicide commercially known as Furadan, at the recommended dosage for the manufacturer.

TABLE 3

| Treatment | Nodulation index | |
|---|---|---|
| Control+ | 5.000 | a |
| Control− | 0.000 | c |
| Furadan | 3.150 | ab |
| BFE | 1.430 | c |

Example 6

Evaluation of Nematicides Bacteria on Plant Parasitic Nematode *Meloidogyne* Populations In Tomato Under Field Conditions in Sandy Loam Soil Conditions Farm La capilla, Boco, Quillota.
Season 2010-2011

In the sector intended for the test, it was used an area, which is free of bromination and other brominated, which determined the design blocks, this in order to compare the effectiveness of the product of the invention with the more efficient commercial product present on the market today.

In each block the following treatments were performed.
T1: Control (no applications)
T2: *Pasteuria penetrans* strain 97 (Pp. 97, which was used as positive control as well as a bionematicide agent.
T3: BFE mixing 3 kg/ha
T4 VYDATE ® (oxamyl) 500 ml/100 l, which was used as as positive control with a chemical nematicide agent.

The applications were made with a backpack sprayer through the bathing of the roots.

Each treatment consisted of 5 repetitions, using 12 plants for treatment.

The initial populations (number of juveniles per 250 g of soil) of *Meloidogyne arenaria* nematodes and *Pratylenchus* sp, predominant in the garden, were determined at the time of applying the treatments and at the end of the harvest.

The data obtained from the study of nematode populations indicate that in both cases, with the use of bromide, as well as without the use of bromide, treatments with *Pasteuria penetrans* strain 97 and BFE mixture as well as VYDATE ® (foxamyl), managed to significantly reduce the populations of *Meloidogyne arenaria*, being the treatment with BFE mixture, the one that showed the highest reduction of populations, showing significant differences with respect to both chemical and biological treatments.

Comparing the final populations, with and without the use of bromide, interaction between treatments and bromide use (P<0.05) was observed, it is interesting to note that all treatments significantly decreased nematode populations, surpassing even the effectiveness of the bromide, with the treatment with the mixture BFE achieving the highest level of control in combination with bromide and that it is able to achieve on its own, the same control as this, being observed the same behavior for both *Meloydigyne* and *Pratyolenchus*, being the latter the one that always displayed the largest populations.

In this case, the growth rate without bromide (FIG. 9) shows a clear trend to the decline in nematode populations.

Budapest Treaty on the International Recognition of the Deposit of Microorganisms for the Purpose of Patent Procedures The microorganisms described in this Application were deposited with the Agricultural Research Service Culture Collection (NRRL), which is an International Depositary Authority, located at 1815 North University Street, Peoria, Ill. 61604, USA.

The deposits were made under the terms of the Budapest Treaty on the International Recognition of the Deposit of Microorganisms for the Purposes of Patent Procedure.

The deposits were made in accordance with, and to satisfy, the criteria set forth in 37 C.F.R. §§1.801-1.809 and the Manual of Patent Examining Procedure §§2402-2411.05.

The NRRL accession numbers and dates of deposit are as follows: *Bacillus cereus* Peumo strain, accession number NRRL B-50767, deposited on Jul. 13, 2012, with the NRRL, *Bacillus cereus* Bromelia strain, accession number NRRL B-50766, deposited on Jul. 13, 2012, with the NRRL; and *Bacillus thuringiensis* Anemophyla strain, accession number NRRL B-50765, deposited on Jul. 13, 2012, with the NRRL.

The invention claimed is:

1. A bionematicide composition, comprising:

a) *Bacillus cereus* Peumo strain (NRRL B-50767), *Bacillus cereus* Bromelia strain (NRRL B-50766), and *Bacillus thuringiensis* Anemophyla strain (NRRL B-50765); and b) an agronomically acceptable vehicle selected from the group consisting of: clay, kaolin, talc, zeolite, water, vegetable oil, and paraffinic or non-paraffinic minerals.

2. The bionematicide composition of claim 1, wherein each strain is in the form of spores.

3. A bionematicide formulation, comprising: the composition according to claim 1, which is formulated in the form of a capsule, a bait, a concentrate, an emulsion, a suspension, a tablet, a gel, a paste, an emulsifiable gel, a dispersible granule, a macrogranule, a microgranule, a powder, or a solution.

4. A method of controlling phytopathogenic nematodes in plants, comprising:

applying a bionematicide composition according to claim 1 to said plants.

5. A method for the control of phytopathogenic nematodes, comprising the steps of:

a) formulating the bionematicide composition according to claim 1; and b) applying said bionematicide formulation to plants, or plant parts, or seeds thereof, where control of phytopathogenic nematodes is desired.

6. A method of controlling phytopathogenic nematodes in plants, comprising:

applying a bionematicide formulation of claim 3 to said plants.

7. The bionematicide composition according to claim 1, wherein the agronomically acceptable vehicle is zeolite.

8. The bionematicide composition according to claim 1, wherein the strains are present at a concentration of at least about $1\times10^8$ CFU/gram.

9. The bionematicide composition according to claim 1, wherein each strain is present in equal proportion.

10. The bionematicide composition according to claim 1, wherein the composition is active against nematodes from the genera *Meloidogyne, Tylenchulus, Pratylenchus, Paratylenchus*, or *Xiphinetna*.

11. A bionematicide composition, comprising:

a) *Bacillus cereus* Peumo strain (NRRL B-50767), *Bacillus cereus* Bromelia strain (NRRL B-50766), and *Bacillus thuringiensis* Anemophyla strain (NRRL B-50765); and b) an agronomically acceptable vehicle selected from the group consisting of: clay, kaolin, talc, zeolite, water, vegetable oil, and paraffinic or non-paraffinic minerals, wherein the three strains are present at a concentration of at least about $1\times10^8$ CFU/gram.

12. The bionematicide composition according to claim 11, wherein each strain is present in equal proportion.

13. The bionematicide composition according to claim 11, wherein the composition is active against nematodes from the genera *Meloidogyne, Tylenchulus, Pratylenchus, Paratylenchus,* or *Xiphinetna*.

14. The bionematicide composition according to claim 11, wherein each strain is in the form of spores.

15. The bionematicide composition according to claim 11, which is formulated in the form of a capsule, a bait, a concentrate, an emulsion, a suspension, a tablet, a gel, a paste, an emulsifiable gel, a dispersible granule, a macrogranule, a microgranule, a powder, or a solution.

16. A bionematicide composition, comprising:
   a) equal proportions of *Bacillus cereus* Peumo strain (NRRL B-50767), *Bacillus cereus* Bromelia strain (NRRL B-50766), and *Bacillus thuringiensis* Anemophyla strain (NRRL B-50765); and
   b) an agronomically acceptable vehicle,
   wherein the three strains are present at a concentration of at least about $1\times10^8$ CFU/gram.

17. The bionematicide composition according to claim 16, wherein the composition is active against nematodes from the genera *Meloidogyne, Tylenchulus, Pratylenchus, Paratylenchus,* or *Xiphinetna*.

18. The bionematicide composition according to claim 16, wherein each strain is in the form of spores.

19. The bionematicide composition according to claim 16, which is formulated in the form of a capsule, a bait, a concentrate, an emulsion, a suspension, a tablet, a gel, a paste, an emulsifiable gel, a dispersible granule, a macrogranule, a microgranule, a powder, or a solution.

20. A bionematicide composition, comprising:
   a) a synergistic combination of *Bacillus cereus* Peumo strain (NRRL B-50767), *Bacillus cereus* Bromelia strain (NRRL B-50766), and *Bacillus thuringiensis* Anemophyla strain (NRRL B-50765); and
   b) an agronomically acceptable vehicle.

21. The bionematicide composition according to claim 20, wherein each strain is present in equal proportion.

22. The bionematicide composition according to claim 20, wherein the composition is active against nematodes from the genera *Meloidogyne, Tylenchulus, Pratylenchus, Paratylenchus,* or *Xiphinetna*.

23. The bionematicide composition according to claim 20, wherein each strain is in the form of spores.

24. The bionematicide composition according to claim 20, which is formulated in the form of a capsule, a bait, a concentrate, an emulsion, a suspension, a tablet, a gel, a paste, an emulsifiable gel, a dispersible granule, a macrogranule, a microgranule, a powder, or a solution.

25. The bionematicide composition according to claim 20, wherein the strains are present at a concentration of at least about $1\times10^8$ CFU/gram.

* * * * *